United States Patent [19]

Bogeso

[11] Patent Number: 4,684,650

[45] Date of Patent: Aug. 4, 1987

[54] ANTIHYPERTENSIVE FLUOROPHENYLINDANYL IMIDAZOLIDINONEETHYLPIPERAZINES

[75] Inventor: Klaus P. Bogeso, Lyngby, Denmark

[73] Assignee: H. Lundbeck A/S, Copenhagen-Valby, Denmark

[21] Appl. No.: 786,199

[22] Filed: Oct. 10, 1985

[30] Foreign Application Priority Data

Oct. 26, 1984 [GB] United Kingdom ............... 8427125

[51] Int. Cl.$^4$ ............... C07D 403/06; C07D 413/06; A61K 31/495
[52] U.S. Cl. ................... 514/252; 544/96; 544/97; 544/360; 544/366; 544/367; 544/369; 544/370; 544/372; 544/374
[58] Field of Search ............. 544/360, 372, 374, 403; 514/252, 255

[56] References Cited

U.S. PATENT DOCUMENTS 4,443,448 4/1984 Bogeso ............... 544/370

Primary Examiner—Mark L. Berch
Assistant Examiner—Cecilia Shen
Attorney, Agent, or Firm—Gordon W. Heuschen

[57] ABSTRACT

The present invention relates to indane derivatives with the following formula:

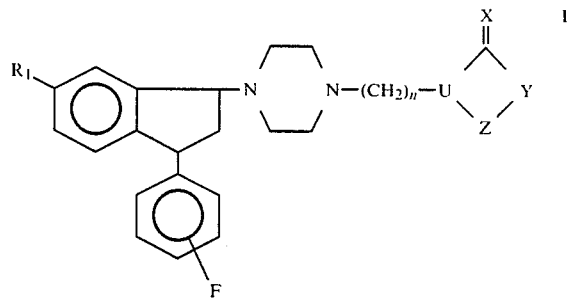

wherein $R_1$ is H, Halogen, an alkyl group having from one to three carbon atoms inclusive, methoxy, a methylthio-group, or a trifluoromethyl group, n is 2–4

X is O or S,

Y is O, $CH_2$ or N—$R_2$, where $R_2$ is hydrogen or an (1–6 C) alkyl, (2–6 C) alkenyl or cycloalkyl-methyl group having from three to six carbon atoms, Z is —$(CH_2)_n$—, n is 2 or 3 or Z is 1,2-phenylene optionally substituted with halogen or trifluoromethyl or Z=1,2—$C_6H_4CO$— (to form a quinazolidinone or -thione ring system). U=N or C.

Each compound exists as geometric isomers and each of these as a pair of optical isomers; and the separation and isolation of these are also within the scope of the invention.

Moreover, pharmaceutically acceptable acid addition salts of the compounds of Formula I are within the scope of the present invention.

Pharmaceutical compositions containing a compound of Formula I or a salt thereof as an active ingredient, and methods for the treatment of hypertension and other cardiovascular diseases as well as anxiety, by administration of a therapeutically active amount of one of the compounds of Formula I to a living animal body, including human beings, fall within the scope of the present invention.

10 Claims, No Drawings

ANTIHYPERTENSIVE FLUOROPHENYLINDANYL IMIDAZOLIDINONEETHYLPIPERAZINES

BACKGROUND OF THE INVENTION

Some of the compounds of Formula I have previously been suggested, e.g. in U.S. Pat. No. 4,443,448, as having among others neuroleptic activity, but such activity was very weak and practically non-existent, meaning that the compounds were found completely without value in the treatment of psychoses and depressions.

It has now surprisingly been found that the compounds of Formula I, of which several are novel compounds, have a high antiserotonergic activity which, together with no neuroleptic activity, make them useful as potential antihypertensive agents. Moreover, such antiserotonergic activity make them of potential interest in the treatment of other cardiovascular diseases such as peripheral vascular diseases, trombolic or embolic episodes, cardiopulmonary emergencies etc. Furthermore, such selective 5HT$_2$-antagonists are potential antianxiety agents.

Only trans-isomers of the claimed compounds are active, cis-isomers being without significant 5-HT$_2$ antagonistic activity. Furthermore, it has been found for the resolved compounds that the 5-HT$_2$ antagonistic activity predominantly resides in the 1R,3S-enantiomers.

Preferred examples of Formula I are compounds wherein $R_1$ is hydrogen or fluorine, n=2, X=O or S, Z=—(CH$_2$)$_2$— and Y=N—R$_2$; R$_2$=H, lower alkyl(-1-3 carbon atoms), as having particularly strong antiserotonergic activity without undesired side effects.

This invention also includes pharmaceutically acceptable salts of the compounds of Formula I formed with non-toxic organic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, oxalic, bis methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

The compounds of Formula I as well as the pharmaceutically acceptable acid addition salts thereof may be administered both orally and parenterally, for example in the form of tablets, capsules, powders, syrups or solutions for injection.

The invention moreover relates to a method for the preparation of the novel indanes of Formula I, which comprises (a) reacting a compound of the following formula II

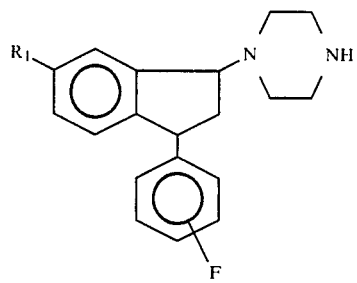

with a compound of formula

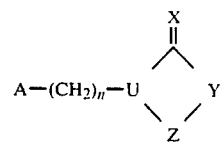

wherein $R_1$, n, X, Y and Z are as defined above, and A is halogen is OSO$_2$R, wherein R is alkyl (e.g. CH$_3$) or aryl (e.g. —C$_6$H$_4$—CH$_3$)

(b) reacting a compound of formula III

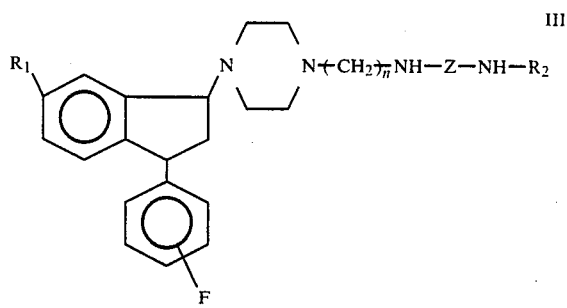

wherein $R_1$, $R_2$, and n are as defined above with urea or with CS$_2$ to give a compound of Formula I, wherein X is O or S respectively, or (c) reacting a compound of formula IV

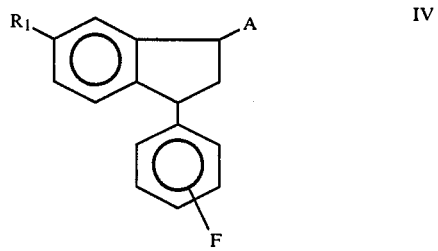

with a compound of formula

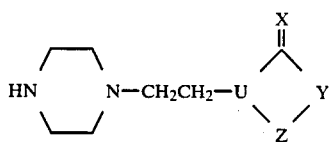

wherein $R_1$, n, X, Y and Z are as defined above, and A is halogen or $OSO_2R$, wherein R is alkyl (e.g. $CH_3$) or aryl (e.g.) —$C_6H_4$—$CH_3$), or (d) reacting a compound of Formula I, wherein X=O with $P_2S_5$ or Lawessons reagent to produce the corresponding compound wherein X is S, whereupon the compound of Formula I is isolated as the free amine or an acid addition salt thereof and, if desired, separated in the individual isomers by conventional means.

The preparation of compounds of formula II and formula IV has been described in U.S. Pat. No. 4,443,448 and in J. Med. Chem. 26, 935 (1983).

Method (a) is preferbly carried out in an inert solvent such as methyl ethylketone or methyl isobutylketone in the presence of an alkali metal carbonate such as potassium carbonate, or another alkaline substance at reflux temperatures.

The compounds of formula

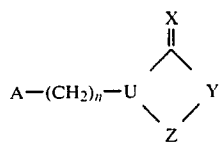

belonging to the chemical classes of 2-imidazolidinones, and -thiones, 2-oxazolidinones and -thiones, 2-pyrrolidinones and -thiones, 2-pyrimidinones and -thiones, benzimidazolidinones and -thiones and 2,4-quinazolidinones and -thiones were prepared according to methods established in the literature.

Method (b) is preferably carried out by treating a compound of Formula III in an inert solvent such as butanol or pentanol with urea or carbondisulfide succeeded by heating at reflux temperatures.

Method (c) is preferably carried out in an inert solvent such as methyl ethylketone or ethanol in the presence of an alkali metal carbonate such as potassium carbonate, or another alkaline substance at reflux temperatures.

Method (d) is preferably carried out in hexamethyl phosphorous triamide (H MPA) or xylene at temperatures between 110° C. and about 200° C.

Optical resolutions of racemic trans-isomers is preferably carried out by fractional crystallization of diastereomeric salts of compound I and optically active acids such as tartaric acid, dibenzoyltartaric acid, mandelic acid etc.

Especially interesting compounds are the following:
(+)Trans-1-[3-(4-fluorophenyl)-indan-1-yl]-4-[2-(2-imidazolidinon-1-yl)ethyl]piperazine.
Trans-1-[3-(4-fluorophenyl)-indan-1-yl]-4-[2-(imidazolidin-2-thion-1-yl)ethyl]piperazine.
(+)Trans-1-[3-(4-fluorophenyl)-6-fluoroindan-1-yl]-4-[2-(2-imidazolidinon-1-yl)ethyl]piperazine.
(+)Trans-1-[3-(4-fluorophenyl)-6-fluoroindan-1-yl]-4-[2-(3-methyl-2-imidazolidinon-1-yl)ethyl]piperazine.
Trans-1-[3-(4-fluorophenyl)-6-chloroindan-1-yl]-4-[2-(2-imidazolidinon-1-yl)ethyl]piperazine, L(+)tartrate.
Trans-1-[3-(4-fluorophenyl)-6-methylindan-1-yl]-4-[2-(2-imidazolidinon-1-yl)ethyl]piperazine.
Trans-1-[3-(4-fluorophenyl)-6-methylthioindan-1-yl]-4-[2-(2-oxazolidinon-3-yl)ethyl]piperazine.

The methods of the invention shall be illustrated in the following by some examples, which may not be construed as limiting:

EXAMPLE 1

Trans-1-[3-(4-fluorophenyl)-indan-1-yl]-4-[2-(2-imidazolidinon-1-yl)ethyl]piperazine and its (+) and (−) enantiomers. (Comp. 1, (+)1 and (−)1)

A mixture of 3-(4-fluorophenyl)-1-chloroindan (103 g, 0.42 mol), piperazine (100 g, 1.2 mol) and potassium iodide in methyl ethylketone (500 ml) was refluxed for 8 hours. After addition of water, the organic phase was separated and evaporated in vacuo. The residue was dissolved in ether and purified by extraction with 2N methane sulfonic acid, followed by liberation of the base with $NH_4OH$. The base was extracted with ether, dried over magnesium sulfate and evaporated in vacuo to give a mixture of trans and cis 1-[3-(4-fluorophenyl)-indan-1-yl]piperazine (101 g, 81%). The base was converted to the maleate with maleic acid in acetone, and the resulting maleate was recrystallized from ethanol. The maleate was then converted to the base to give an almost pure trans-isomer of the abovementioned compound (54 g).

A mixture of this trans-isomer (54 g, 0.18 mol), 1-(2-chloroethyl)-imidazolidin-2-one (29 g, 0.20 mol), potassium carbonate (30 g) and potassium iodide (2 g) in methyl isobutylketone (300 ml) was refluxed for 14 hours. After addition of water the organic phase was separated and evaporated in vacuo. The residue was dissolved in dilute acetic acid, extracted once with ether (which was rejected), whereupon the base was liberated with $NH_4OH$ and extracted with methylene chloride.

After drying over magnesium sulfate and evaporation in vacuo the residue was crystallized from ethyl acetate-diisopropyl ether to give compound 1 (37 g); mp. 153°–157° C.

A mixture of compound 1 (37 g, 0.091 mol) and (−)0,0'-dibenzoyl-L-tartaric acid, hydrate (34 g, 0.091 mol) in methanol (300 ml) was heated until a clear solution was obtained. The mixture was crystallized in a refrigerator for 5 hours, and filtered, whereupon the salt was recrystallized from ethyl acetate-methanol to give (+)1, (−)-dibenzoyltartaric acid salt, hydrate; mp.: 131°–133° C., $[\alpha]_D = -24.6°$ (c=5, dimethyl formamide).

The salt was converted to the base with $NH_4OH$, which was extracted with ethyl acetate, dried over magnesium sulfate and evaporated in vacuo. The residue was crystallized from ether-diisopropylether to give (+)trans-1-[3-(4-fluorophenyl]indan-1-yl]-4-[2-(2-imidazolidinon-1-yl)ethyl]piperazine ((+)1, 14 g) mp.: 94°–97° C., $[\alpha]_D = +16.0°$ (c=4, methanol). Karl-Fisher titration: 0.3% $H_2O$.

CHN calc.: 70.34%; 7.18%; 13.68%
CHN found: 70.58%; 7.40%; 13.39%

The first filtrate from the (−)dibenzoyltartaric acid salt was evaporated in vacuo and converted to the base (20.6 g) which was treated with a solution of (+)0,0'-dibenzoyl-D tartaric acid, hydrate (19 g) in methanol. After crystallization the salt was filtered and recrystallized from ethyl acetate-methanol to give the (+)dibenzoyltartaric acid salt of (−)1. Mp: 135°–138° C., $[\alpha]_D = +22°$ (c=5, DMF).

The salt was converted to the base which was crystallized from diisopropylether to give (−)trans-2-3-(4-fluorophenyl)-indan-1-yl-4-2-(2-imidazolidinon-1-yl)ethyl piperazine ((−)1, 9.5 g). Mp: 84°–86° C., $[\alpha]_D = -15.7°$ (c=4, methanol). Karl-Fisher titration 1.1% $H_2O$.

CHN calc.: 69.77%; 7.21%; 13.57%

CHN found: 69.77%; 7.17%; 13.35%

In a corresponding manner the following indane derivatives (Table 1) were made, which are all trans-isomers and all having the obligatory fluorine atom in the 4-position:

residue, whereupon the mixture was refluxed for 1 hour with evolution of hydrogen sulfide.

After evaporation in vacuo the residue was dissolved in ether, which was washed with water, whereupon the base was purified by extraction with 1N methanesul-

TABLE 1

| Compd. | $R_1$ | n | X | Y | Z | salt/base | Mp. °C | Specific rotation |
|---|---|---|---|---|---|---|---|---|
| U = N | | | | | | | | |
| 2 | F | 2 | O | NH | —(CH$_2$)$_2$— | base | 149–151 | |
| (+)2[10] | F | 2 | O | NH | —(CH$_2$)$_2$— | dimaleate | 172–74 | $[\alpha]_D^{22} = +10.4°$ (C = 5,DMF) |
| (−)2 | F | 2 | O | NH | —(CH$_2$)$_2$— | dimaleate | 172–74 | $[\alpha]_D^{22} = -10.7°$ (C = 5,DMF) |
| 3 | F | 2 | O | NCH$_3$ | —(CH$_2$)$_2$— | diHCl | 239–41 | |
| (+)3[10] | F | 2 | O | NCH$_3$ | —(CH$_2$)$_2$— | base | 91–92 | $[\alpha]_D^{22} = +11.2°$ (C = 5,MeOH) |
| (−)3[10] | F | 2 | O | NHC$_3$ | —(CH$_2$)$_2$— | base | 92–93 | $[\alpha]_D^{22} = -10.6°$ (C = 5,MeOH) |
| 4 | CH$_3$ | 2 | O | NH | —(CH$_2$)$_2$— | base | 165–68 | |
| 5 | (CH$_3$)$_2$CH | 2 | O | NH | —(CH$_2$)$_2$— | diHCl | 285–88 | |
| 6 | CF$_3$ | 2 | O | NH | —(CH$_2$)$_2$— | diHCl | 275–77 | |
| 7 | H | 2 | O | O | —(CH$_2$)$_2$— | diHCl | 227–29 | |
| 8 | F | 2 | O | O | —(CH$_2$)$_2$— | diHCl, H$_2$O | 220–23 | |
| 9 | CH$_3$ | 2 | O | O | —(CH$_2$)$_2$— | base | 111–12 | |
| 10 | CH$_3$S | 2 | O | O | —(CH$_2$)$_2$— | diHCl | 213–15 | |
| 11 | H | 2 | O | NCH$_3$ | —(CH$_2$)$_2$— | diHCl | 236–38 | |
| 12 | F | 2 | O | N—C$_2$H$_5$ | —(CH$_2$)$_2$— | diHCl | 248–50 | |
| 13 | F | 2 | O | N—CH(CH$_3$)$_2$ | —(CH$_2$)$_2$— | diHCl | 250–53 | |
| 14 | F | 3 | O | NH | —(CH$_2$)$_2$— | diHCl | 239–42 | |
| 15 | F | 3 | O | O | —(CH$_2$)$_2$— | diHCl | 227–30 | |
| 16 | F | 2 | O | NH | 1,2-C$_6$H$_4$— | diHCl | 248–51 | |
| 17 | F | 2 | O | NH | 1,2-COC$_2$H$_4$—Y— | base | 210–12 | |
| 18 | F | 2 | O | CH$_2$ | —(CH$_2$)$_2$— | diHCl | 260–63 | |
| 19 | H | 2 | O | NH | 1,2-COC$_6$H$_4$—Y— | diHCl | 217–220 | |
| (+)20 | Cl | 2 | O | NH | —(CH$_2$)$_2$— | L(+)-tartrate | 203–205 | $[\alpha]_D^{22} = -12.2°$ (C = 1,MeOH) |
| (−)20 | Cl | 2 | O | NH | —(CH$_2$)$_2$— | D(−)-tartrate | 203–205 | $[\alpha]_D^{22} = +12.5°$ (C = 1,MeOH) |
| 21 | Cl | 2 | O | CH$_2$ | —(CH$_2$)$_2$— | base | 142–144 | |
| 22 | Cl | 2 | O | O | —(CH$_2$)$_2$— | base | 113–114 | |
| U = C | | | | | | | | |
| 23 | H | 2 | O | NCH$_3$ | —(CH$_2$)$_2$— | dimaleate | 172–74 | |

EXAMPLE 2

Trans-1-[3-(4-fluorophenyl)-6-fluoroindan-1-yl]-4-[2-(2-imidazolidinthion-1-yl)ethyl]piperazine and its (+) enantiomer (Compd. (±)19 and (+)19).

A mixture of trans-4-[3-(4-fluorophenyl)-6-fluoro-indan-1-yl]-1-piperazineethanol (40 g, 0.11 mol), thionylchloride (15 ml) and DMF (0.7 ml) in methylene chloride (400 ml) was refluxed for 1 hour. After cooling, the crystalline solid was filtered and washed on the filter with ethyl acetate and ether to give trans 1-[3-(4-fluorophenyl)-indan-1-yl]-4-(2-chloroethyl)piperazine, dihydrochloride (45 g). Mp: 250°–255° C.

A mixture of this dihydrochloride (20 g) and ethylendiamine (50 g) in ethanol (200 ml) was refluxed for 2 hours and then evaporated in vacuo. To the residue was added water and methylene chloride. The organic phase was washed with water, dried over magnesium sulfate and evaporated in vacuo to give trans-1-[3-(4-fluorophenyl)-6-fluoro-indan-1-yl]-4-[2-(2-aminoethyl)amino)ethyl]piperazine as an oil (19 g). Tetramaleate, Mp: 158°–162° C.

To a solution of the ethylendiamine derivative (19 g) in ethanol (100 ml) and methylene chloride (100 ml) was added carbon disulfide (5 ml), and the mixture was kept at room temperature for 2 hours. After evaporation in vacuo, n-pentanol (200 ml) was added to the crystalline fonic acid followed by reprecipitation with NH$_4$OH. The purified base was extracted with ether, dried over magnesium sulfate and evaporated in vacuo. The residue (18 g) was recrystallized from isopropylether-methylene chloride to give comp. (±)19 (11 g). Mp: 138°–142° C.

CHN calc.: 64.91%; 6.37%; 12.62%
CHN found: 64.90% 6.31%; 12.56%

To a solution of comp. (±)19 (17 g) in ethanol (200 ml) was added a solution of L(+)tartaric acid in ethanol (50 ml), whereupon the mixture was allowed to stand at room temperature for 16 hours. The salt was filtered and recrystallized from methanol (250 ml) to give the L(+)tartaric acid salt of (+)19, MP: 218°–219° C. The salt was converted to the base (NH$_4$OH/methylene chloride), which again was converted to the dimaleate. Mp: 166°–169° C. This maleate was recrystallized twice from ethanol to give (+)19, dimaleate, MP: 175°–177° C., $[\alpha]_D = +5.9°$ (c=1, methanol).

CHN calc.: 56.98%; 5.39%; 8.31%
CHN found: 57.58%; 5.06%; 8.19%.

In a manner corresponding to the procedure given in Example 2, the following trans-indane derivatives were made (see Table 2)—(in the cases where X=O, carbondisulfide is substituted with urea in the preparation procedure)—and all having the obligatory fluorine atom in the 4-position:

TABLE 2

| Compd. | R₁ | n | X | Y | Z | salt/base | Mp. °C | Specific rotation |
|---|---|---|---|---|---|---|---|---|
| 24 | F | 2 | S | NH | —(CH$_2$)$_2$— | base | 138-42 | |
| (+)24 | F | 2 | S | NH | —(CH$_2$)$_2$— | dimaleate | 175-77 | $[\alpha]_D^{22} = -5.9°$ (C = 1, CH$_3$OH) |
| 25 | F | 2 | O | NH | —(CH$_2$)$_3$— | dimaleate | 163-67 | |
| 26 | F | 2 | S | NH | —(CH$_2$)$_3$— | diHCl | 187-89 | |
| 27 | H | 2 | S | NH | —(CH$_2$)$_2$— | dimaleate | 178-80 | |
| 28 | Cl | 2 | S | NH | —(CH$_2$)$_2$— | base | 154-156 | |

EXAMPLE 3

(+)Trans-1-[3-(4-fluorophenyl)-indan-1-yl]-4-[2-(2-imidazolidinon-1-yl)ethyl]piperazine, L(+)tartrate. (comp. (+)1).

A mixture of piperazine (86 g, 1.0 mol), 1-(2-chloroethyl)-imidazolidin-2-one (74 g, 0.5 mol) and sodium carbonate (159 g, 1.5 mol) in ethanol (500 ml) was refluxed with stirring for 1.5 hours. A solution of 1-(2-chloroethyl)-imidazolidin-2-one (74 g, 0.5 mol) in methanol (75 ml) was then added in the course of 1.5 hours, at reflux temperature, whereupon the reaction mixture was refluxed for 18 hours. After cooling, the reaction mixture was filtered and evaporated in vacuo. The residue was dissolved in hot ethanol (100 ml), whereupon ethyl acetate (200 ml) was added. The crystals were filtered and dried to give 1-(2-(2-imidazolidinon-1-yl)ethyl)piperazine (60 g) mp. 136°-140° C. Additional 22 g could be obtained from the mother liquor.

A mixture of 3-(4-fluorophenyl)-1-chloroindan (92 g, 0.37 mol), 1-(2-(2-imidazolidinon-1-yl)ethyl)piperazine (81 g, 0.41 mol), potassium carbonate (70 g, 0.5 mol) and potassium iodide (1 g) in methyl ethylketone (500 ml) was refluxed for 18 hours. The reaction mixture was cooled, filtered and evaporated in vacuo. The residue was dissolved in ether and purified by extraction with dilute acetic acid, followed by liberation of the base with 10N sodium hydroxide. The base was extracted with methylene chloride, dried over magnesium sulfate and eveporated in vacuo. The resulting oil was dissolved in ethyl acetate (120 ml), whereupon diisopropylether (360 ml) was added. After crystallization in a refrigerator for 18 hours the crystals were filtered and dried to give a cis-trans mixture of racemic 1-[3-(4-fluorophenyl)-indan-1-yl]-4-[2-(2-imidazolidinon-1-yl)ethyl]piperazine (140 g) mp. 141°-145° C.

To a slurry of the racemic cis-trans mixture in methanol (1.5 liters) was added a solution of L(+)tartaric acid (51 g, 0.34 mol) in methanol (1 liter). The resulting solution was stirred for 18 hours at room temperature. The crystals were filtered, washed with methanol and acetone and dried to give crude (+)1 (60 g) mp. 217°-219° C. The tartrate was recrystallized twice from water-methanol 5:1 to give pure (+)1, L(+)tartrate (50 g); mp. 226°-227° C. $[\alpha]_D^{22} = +29.6°$ (c=0.7, H$_2$O).

EXAMPLE 4

(±)Trans-1-[3-(4-fluorophenyl)-6-chlorindan-1-yl]-4-[2-(2-pyrrolidinthion-1-yl)ethyl]piperazine, Comp. 29.

A mixture of Comp. 21 (4.4 g, 0.01 mol) and 2,4-bis(4-methoxyphenyl)-1,3-dithia-2,4-diphosphetane-2,4-disulfide (Lawessons Reagent, 6 g, 0.015 mol) in HMPA (30 ml) was heated with stirring at 110° C. for 1 hour. The reaction mixture was then poured into water (400 ml) and 9N NaOH (50 ml) and extracted with ether. The base was extracted from the ether phase with 1N methanesulfonic acid and reprecipitated with NH$_4$OH. The base was again extracted with ether, dried over magnesium sulfate and evaporated in vacuo. The crystalline residue was recrystallized from ether/isopropylether to give comp. 31 (2.5 g) Mp: 122°-124° C.

CHN calc.: 65.55%; 6.39%; 9.18%.
CHN found: 65.54%; 6.50%; 8.91%.

PHARMACOLOGY

The activites of the compounds in the following tests—which are reliable and wellknown in the art—will appear from Table 3.

Methylphenidate Antagonism

The experiments were made as described by Pedersen and Christensen (1972) Acta Pharmacol. et Toxicol. 31, 488-496.—Briefly, test compounds or saline were injected i.p. 2 hours before methylphenidate, 60 mg/kg s.c. 3 pairs of mice were used for each dose level. After methylphenidate injection the mice were placed in observation cages for one hour. The cages were placed on corrugated paper, the corrugation facing upwards. The number of pairs that did not bite the corrugated paper were recorded as protected against methylphenidate; and ED$_{50}$ values were determined by log-probit analysis.

1-5-HTP-induced head shakes

The rats were pretreated subcutaneously with test compound or saline simultaneously with or 90 min before injection of citalopram (10 mg/kg s.c.). Fifteen minutes later (1-5-HTP (75 mg/kg i.p.) was administered. The rats were then placed individually in perspex observation cages (12×25 cm), and in standard experiments the number of head shakes (involving the head and sometimes part of the body) were counted for 10 min., 30-40 min. after 1-5-HTP, where the effect was maximal. The number of rats showing 0-1 head shakes were considered as protected (90 percent reduction compared with daily controls), and ED$_{50}$ values were calculated by log-probit analysis of results from at least 3 doses.

Each group consisted of 4-12 rats.

Quipazine-induced head shakes

The rats were pretreated subcutaneously with test compound or saline 2 hours before injection of quipazine (5 mg/kg s.c.). The rats were then placed individually in perspex observation cages (12×25 cm), and in standard experiments the number of head shakes (involving the head and sometimes part of the body) were counted for 10 min., 30-40 min. after quipazine, where the effect was maximal. The number of head shakes in each dose group were expressed in percent of those induced in the control group, and ED$_{50}$ values were calculated by log-probit analysis of results from at least 3 doses.

Each group consisted of 4-12 rats.

$^3$H-spiroperidol binding to 5-HT$_2$ receptors.

Rat whole cortex was homogenized by an Ultra Turrax homogenizer in 100 vol. of 50 mM Tris buffer pH 7.7. The homogenate was centrifuged at 20,000 g for 10 minutes at 4° C. The pellet was rehomogenized in another volume of buffer and centrifuged as mentioned above. The final pellet was rehomogenized in 50 mM Tris buffer pH 7.7 containing 120 mM NaCl, 5 mM KCl, 2 mM $CaCl_2$ and 1 mM $MgCl_2$ (ion mix) in a volume corresponding to 12.5 mg original tissue per ml.

Test drugs were dissolved in water; $^3$H-spiroperidol (NEN, 28–30 Ci/mmol) was diluted in 3 μM sulpiride, and 800 μl membrane suspension were added. Final concentration of ligand and sulpiride were 0.5 nM and 0.3 μM, respectively. The samples were incubated at 37° C. for 10 min. The samples were then filtered under vacuum through Whatman GF/B glass-fiber filters. The tubes were then rinsed with 5 ml incubation buffer, which was poured on the filters. The filters were finally washed twice with 5 ml buffer and placed in counting vials. After addition of 5 ml scintillation fluid (Lumagel) radioactivity was estimated by liquid scintillation counting. Non-specific binding was obtained by adding Mianserin (1 μM) to separate samples. Each drug was tested at least twice at 5 concentrations in triplicate. IC50-values were determined from log concentration-response curves.—The presence of sulpiride excluded binding to dopamine D-2 receptors.

Antihypertensive effect in spontaneous hypertensive rats (SHR)

The femoral artery of male SHR is cannulated in anaesthesia for blood pressure recordings. After a stabilization period of 1½ h after discontinuation of the anaesthesia initial blood pressure curves are recorded and the systolic (SAP)/diastolic (DAP) pressure determined (−20, −10, 0, min. p.i.) Test substance is injected i.p. and the pressure curve recorded for one hour. The change in SAP/DAP is calculated in percent at mean initial values at different times (10, 20, 30, 40, 50 and 60 minutes after injection). At least two SHR are used per dose level. The maximum change is used for estimation of the drug effect.

Antagonism to 5-HT or phenylephrine pressor responses in pithed rats.

The rat is anaesthetized with ether, tracheotomized, artificial respired and pithed. The knitting-needle is introduced through the right orbita into the cranial cavity and passed through foramen magnum into the spinal canal as far as possible. The spinal cord is destroyed by turning the needle. After vagotomi both carotides are ligated and a catheter placed in the right one for pressure recording. The rat is adrenalectomized. The drugs are injected into the left jugular vein, with intervals of 15 minutes, in the following sequence:

2×pressor substance, followed by 3–4 dose levels of test substance (1 dose/rat), thereupon 2×pressor substance.

The initial and post medication mean pressor effect is calculated, and the mean pressor effect is calculated as % of the initial value. Two to five preparations are employed for each dose level. The $ED_{50}$ is determined.

Antihypertensive Effects

Many of the drugs showed potent antihypertensive action. (Table 3, SHR). Among those drugs are some which mainly possess periferal action (i.e. +1, 14) in contrast with many others, including tefludazine, with marked central effects (13, 12). In addition to the 5-HT antagonistic effect some of the drugs possess strong alpha-adrenolytic effects (phenylephrine antagonism, pithed rat) resulting in only moderate ratios between phenylephrine antagonism and 5-HT antagonism. To avoid indesirable side effects perepherally acting, potent 5-HT antagonists with weak adrenolytic and central effect are considered advantages as antihypertensive drugs.

As can be seen from the table, all compounds are very weak or inactive against methylphenidate induced stereotypies, in contrast with the high activity found for (±)trans-4-[3-(4-fluorophenyl)-6-(trifluoromethyl)-indan-1-yl]-1-piperazineethanol (Tefludazine) in this test. In contrast with this low antistereotypic activity all compounds or potent antagonists of 1-5-HTP induced head-twitches.

TABLE 3

| Compd. | MePh antg. $ED_{50}$ μmol/kg i.p. | 1-5-HTP-antg. $ED_{50}$ μmol/kg s.c. | $^3$H-SPI binding 5-HT$_2$ IC$_{50}$ (nM) | Antihypertensive eff. SHR max eff. in % of 5 mg/kg ip SAP/DAP | $ED_{10}$ μmol/kg SAP | $ED_{10}$ μmol/kg DAP | 5-HT % eff. of 0.02 mg/kg | 5-HT $ED_{50}$ μmol/kg | Phenylephrine % eff. of 0.31 mg/kg | Phenylephrine $ED_{50}$ μmol/kg | Phenylephr. antg. 5-HT antg. |
|---|---|---|---|---|---|---|---|---|---|---|---|
| 1 | >98 | 1.3 | 25 | −33/−43 | 5.9 | 4.2 | −68 | 0.024 | −30 | 3.13 | 130 |
| +1 | >97 | 1.5 | 6 | −33/−47 | 1.7 | 1.2 | −81 | 0.009 | −14 | 3.21 | 357 |
| −1 | >97 | 8.9 | 130 | −3/−11 | | | −11 | | +53 | | |
| 2 | (79) | 0.13 | 6.7 | −14/−19 | 9.2 | 4.1 | −89 | 0.017 | −27 | 2.55 | 150 |
| +2 | >61 | 0.10 | 4.3 | −31/−40 | 1.6 | 0.8 | | 0.010 | −14 | 1.43 | 143 |
| −2 | >61 | 20 | 320 | +6/+4 | | | +2 | 1.43 | +11 | | |
| 3 | >78 | 0.08 | 3.4 | −11/−13 | | | −87 | 0.010 | −12 | 14.0 | 1400 |
| +3 | >91 | 0.023 | 1.1 | −38/−52 | | | −89 | 0.004 | −3 | 2.25 | 563 |
| −3 | >91 | 45 | 410 | I | | | −6 | | +72 | | |
| 4 | 27 | 0.13 | 23 | −27/−32 | 3.3 | 2.4 | −73 | 0.017 | −38 | 2.02 | 119 |
| 5 | 24 | 1.7 | NT | −9/−10 | | | −6 | | −33 | | |
| 6 | 1.8 | 0.29 | 9.9 | −10/−14 | | | −52 | | −32 | | |
| 7 | >83 | 2.7 | NT | −15/−19 | | | −4 | | −18 | | |
| 8 | 18 | 1.3 | NT | −20/−26 | | | −40 | 0.084 | −19 | 4.35 | 52 |
| 9 | 29 | 0.45 | 21 | −32/−41 | 4.5 | 3.5 | −73 | 0.020 | −40 | 1.51 | 76 |
| 10 | >76 | 2.4 | 6.6 | −14/−22 | | | −57 | 0.034 | −25 | 9.4 | 276 |
| 11 | >80 | 1.4 | 13 | −6/−8 | | | −81 | | +6 | | |
| 12 | >75 | 0.092 | 4.9 | +4/+4 | | | −94 | | −9 | | |
| 13 | >73 | 0.11 | 5.2 | −5/−5 | | | −79 | | −5 | | |
| 14 | 56 | 2.0 | 6.3 | −12/−19 | | | −68 | 0.031 | −28 | 2.68 | 86 |
| 15 | 39 | 0.31 | NT | −12/−18 | | | −31 | | −7 | | |
| 16 | >72 | 0.28 | 9.7 | −15/−11 | | | −52 | | −21 | | |
| 17 | >79 | 10 | 3.0 | −29/−46 | | | −52 | | −57 | | |
| 18 | 18 | 0.76 | 12 | I | | | −67 | | −28 | | |

TABLE 3-continued

| Compd. | MePh antg. ED$_{50}$ μmol/kg i.p. | 1-5-HTP-antg. ED$_{50}$ μmol/kg s.c. | $^3$H-SPI binding 5-HT$_2$ IC$_{50}$ (nM) | Antihypertensive eff. SHR max eff. in % of 5 mg/kg ip SAP/DAP | ED$_{10}$ μmol/kg SAP | DAP | Effects on pressor response of 5-HT or Phenylephrine in pithed rats 5-HT % eff. of 0.02 mg/kg | ED$_{50}$ μmol/kg | Phenylephrine % eff. of 0.31 mg/kg | ED$_{50}$ μmol/kg | Phenylephr. antg. 5-HT antg. |
|---|---|---|---|---|---|---|---|---|---|---|---|
| 19 | >70 | NT | NT | −22/−27 | | | −35 | | −42 | | |
| +20 | 49 | 0.028 (Q) | NT | −29/−45 | | | −92 | | −34 | | |
| −20 | >67 | <8.4 | NT | −7/−16 | | | −11 | | +21 | | |
| 21 | 11 | 0.079 (Q) | NT | −11/−14 | | | −83 | | +3 | | |
| 22 | 2.8 | 0.12 (Q) | NT | −17/−21 | | | −77 | | −5 | | |
| 23 | >61 | 1.4 | 16 | −31/−43 | | | −38 | | −82 | | |
| 24 | 25 | 0.13 | 5.2 | −10/−20 | | | −88 | 0.010 | −5 | 3.7 | 370 |
| +24 | 17 | 0.03 | 2.5 | −32/−40 | | | −88 | | −2 | | |
| 25 | >59 | 1.2 | 12 | I | | | −60 | | −1 | | |
| 26 | NT | 0.11 | 7.7 | −13/−19 | | | −67 | | −7 | | |
| 27 | >61 | 0.48 | 4.7 | −18/−29 | | | −71 | | −9 | | |
| 28 | 4.5 | 0.017 (Q) | NT | −6/−10 | | | −93 | | −22 | | |
| 29 | NT | <0.17 (Q) | NT | −5/−4 | | | −88 | | +8 | | |
| Ketanserin | 101 | 0.58 | 2.1 | −32/−24 | 1.6 | 1.2 | −46 | 0.033 | −44 | 3.6 | 109 |
| Tefludazine | 0.06 | 0.039 | 8.6 | −18/−24 | | | −78 | 0.015 | −27 | 1.7 | 115 |

I = Inactive
NT = Not Tested
Q = Quipazine antg.

The compounds of Formula I and the non-toxic acid addition salts thereof may be administered to animals such as dogs, cats, horses, sheep or the like, including human beings, both orally and parenterally, and may be used for example in the form of tablets, capsules, powders, syrups—or in the form of the usual sterile solutions for injection.

Results upon administration to human beings have been very gratifying.

Most conveniently the compounds of Formula I are administered orally in unit dosage form such as tablets or capsules, each dosage unit containing a non-toxic acid addition salt of one of said compounds in an amount of from about 0.10 to about 100 mg, most preferably, however, from about 5 to 50 mg, calculated as the free amine, the total daily dosage usually ranging from about 1.0 to about 500 mg.—The exact individual dosages as well as daily dosages in a particular case will, naturally, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums or the like.

Typical examples of formulas for composition containing (+)trans-1-[3-(4-fluorphenyl)-indan-1-yl]-4-[2-(2-imidiazolidinon-1-yl)ethyl]piperazine hydrate (called Lu 21-098 X for short) as the active ingredient, are as follows:

(1) Tablets containing 5 milligrams of Lu 21-098 X calculated as the free base:

| | |
|---|---|
| Lu 21-098 X | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

(2) Tablets containing 50 milligrams of Lu 21-098 X calculated as the free base:

| | |
|---|---|
| Lu 21-098 X | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |

(3) Syrup containing per milliliter:

| | |
|---|---|
| Lu 21-098 X | 10 mg |
| Sorbitol | 500 mg |
| Tragacanth | 7 mg |
| Glycerol | 50 mg |
| Methyl-paraben | 1 mg |
| Ethanol | 0.005 ml |
| Water | ad 1 ml |

(4) Solution for injection containing per milliliter:

| | |
|---|---|
| Lu 21-098 X | 50 mg |
| Acetic acid | 17.9 mg |
| Sterile water | ad 1 ml |

(5) Solution for injection containing per milliliter:

| | |
|---|---|
| Lu 21-098 X | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided they are compatible with the active ingredient.

Also combinations of the compounds of Formula I as well as their non-toxic acid salts with other active ingredients fall within the scope of the present invention.

As previously stated, when isolating the compounds of Formula I in the form of an acid addition salt, the acid is preferably selected so as to contain an anion which is non-toxic and pharmaceutically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, embonates and maleates of the amines of Formula I. Other acids are likewise suitable and may be employed if desired. For example: Fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent, drying the extract and evaporating to dryness, or fractionally distilling to effect isolation of the free basic amine.

The invention also comprises a method for the alleviation, palliation, mitigation, or inhibition of the manifestations of certain physiological-psychological abnormalies of animals, including hypertension, cardiovascular diseases, anxiety or the like, by administering to a living animal body—including human beings—an adequate quantity of a compound of Formula I or a non-toxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact compound or compositions shown and described, as obvious medifications and equivalents will be apparent to one skilled in the art.

I claim:

1. A compound selected from the group consisting of
(a) a 1-piperazine-3-phenylindane of the formula:

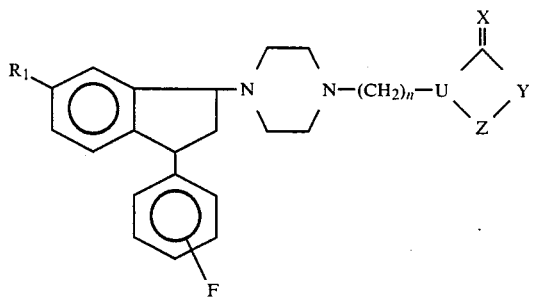

wherein $R_1$ is selected from H, halogen, an alkyl group having from one to three carbon atoms inclusive, a methoxy group, a methylthio group and a trifluoromethyl group,
n is 2–4
X is selected from O and S,
Y is selected from O, $CH_2$ and N—$R_2$, where $R_2$ is selected from hydrogen, and (1–6 C)alkyl, (2–6 C)alkenyl and a cycloalkyl-methyl group having from three to six carbon atoms,
Z is selected from —$(CH_2)_n$, wherein n is 2, and 1,2-phenylene optionally substituted with a group selected from halogen and trifluoromethyl,
U is selected from N and C, with the proviso that when X is O, Y is selected from O and NH, U is N, Z is —$(CH_2)_2$, $R_1$ may not be a group selected from halogen, an alkyl group having from one to three carbon atoms inclusive, a methoxy group, a methylthio-group and a trifluoromethyl group, and
(b) a pharmaceutically acceptable acid addition salt thereof.

2. A compound according to claim 1, wherein $R_1$ is hydrogen, n=2, X is selected from O and S, Z=—$(CH_2)_2$, Y=N—$R_2$ wherein $R_2$ is selected from hydrogen and lower alkyl(1–3 C-atoms).

3. A compound according to claim 1, selected from the following named compounds:
(+)Trans-1-[3-(4-fluorophenyl)indan-1-yl]-4-[2-(2-imidazolidinon-1-yl)-ethyl]piperazine,
Trans-1-[3-(4-fluorophenyl)indan-1-yl]-4-[2-(imidazolidin-2-thion-1-yl)-ethyl]piperazine,
(+)Trans-1-[3-(4-fluorophenyl)indan-1-yl]-4-[2-(3-methyl-2-imidazolidinon-1-yl)-ethyl]piperazine, or a pharmaceutically acceptable salt thereof.

4. A pharmaceutical composition, suitable for treatment of hypertension, in unit dosage form comprising—as an active ingredient—an effective antihypertensive amount of a compound as defined in claim 1, and one or more pharmaceutical diluents or carriers.

5. A pharmaceutical composition in unit dosage form, according to claim 4, wherein the active ingredient is present in an amount from 0.10 to 100 milligrams per unit dosage.

6. A pharmaceutical composition according to claim 4 or 5, comprising as an active ingredient a compound as defined in claim 3.

7. A method for the treatment of hypertension, comprising administering an effective antihypertensive amount of a compound selected from the group consisting of
(a) a 1-piperazine-3-phenylindane of the formula:

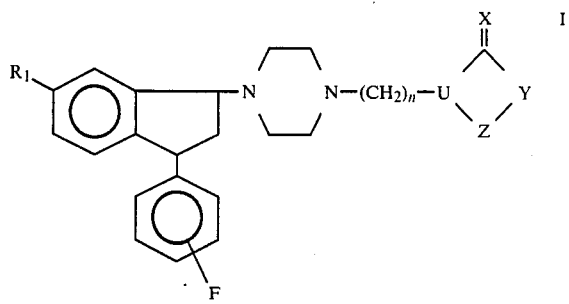

wherein
$R_1$ is selected from H, halogen, an alkyl group having from one to three carbon atoms inclusive, a methoxy group, a methylthio group and a trifluoromethyl group,
n is 2–4
X is selected from O and S,
Y is selected from O, $CH_2$ and N—$R_2$, where $R_2$ is selected from hydrogen, and (1–6 C)alkyl, (2–6 C)alkenyl and a cycloalkyl-methyl group having from three to six carbon atoms,
Z is selected from —$(CH_2)_n$, wherein n is 2, and 1,2-phenylene optionally substituted with a group selected from halogen and trifluoromethyl,
U is selected from N and C, and
(b) a pharmaceutically acceptable acid addition salt thereof or an individual isomer thereof, as an active ingredient, and one or more pharmaceutical diluents or carriers, to a warmblooded animal, including a human being.

8. A method according to claim 7, wherein the active ingredient is present in an amount from 0.10 to 100 milligrams per unit dosage.

9. A method according to claim 7 or 8, wherein the active ingredient is (+)trans-1-[3-(4-fluorophenyl)- indan-1-yl]-4-[2-(2-imidazolidinon-1-yl)ethyl]piperazine or a pharmaceutically acceptable acid addition salt thereof.

10. A method according to claim 7 or 8, wherein the active ingredient is selected from the group consisting of:

(30) Trans-1-[3-(4-fluorophenyl)indan-1-yl]-4-[2-(2-imidazolidinon-1-yl)ethyl]piperazine,
Trans-1-[3-(4-fluorophenyl)indan-1-yl]-4-[2-imidazolidin-2-thion-yl)ethyl]piperazine, and
Trans-1-[3-(4-fluorophenyl)indan-1-yl]-4-[2-(3-methylimidazolidinon-1-)-ethyl]piperazine,
or a pharmaceutically-acceptable salt of any of the foregoing named compounds.

* * * * *

UNITED STATES PATENT AND TRADEMARK OFFICE
CERTIFICATE OF CORRECTION

PATENT NO. : 4,684,650

DATED : August 4, 1987

INVENTOR(S) : Klaus P. Bogeso

It is certified that error appears in the above-identified patent and that said Letters Patent is hereby corrected as shown below:

Title Page, on the same line as "Attorney, Agent, or Firm";
  "Heuschen" should read -- Hueschen --
Col. 2, line 26; "is halogen is" should read -- is halogen or --
Col. 2, line 27; after "(e.g. $-C_6H_4-CH_3$)" insert -- or --
Cols. 5&6, TABLE 1, Col. 1, line 3; "$(+)2^{10}$" should read -- $(+)2$ --
Cols. 5&6, TABLE 1, Col. 1, line 6; "$(+)3^{10}$" should read -- $(+)3$ --
Cols. 5&6, TABLE 1, Col. 1, line 7; "$(-)3^{10}$" should read -- $(-)3$ --
Cols. 7&8, TABLE 2, last column, first line; "$-5.9°$" should read -- $+5.9°$ --
Col. 8, lines 20&21; "test-      should      -- tests -
                      s-which"    read         which --
Col. 14, lines 13&14; "comprisin-  should     -- comprising -
                       g-as"       read        as --
Col. 16, line 1; "(30)Trans-" should read -- (+) Trans- --

Signed and Sealed this

Twelfth Day of April, 1988

Attest:

DONALD J. QUIGG

Attesting Officer

Commissioner of Patents and Trademarks